United States Patent
Hernandez et al.

(10) Patent No.: US 9,987,254 B2
(45) Date of Patent: Jun. 5, 2018

(54) OPHTHALMIC COMPOSITION FOR CORRECTING PRESBYOPIA

(71) Applicant: Eurocanarias Oftalmológica, S.L., Las Palmas de Gran Canaria (ES)

(72) Inventors: Jose Vincent Rodriguez Hernandez, Las Palmas de Gran Canaria (ES); Humberto Carreras Diaz, Las Palmas de Gran Canaria (ES)

(73) Assignee: EUROCANARIAS OFTALMOLÓGICA, S.L., Las Palmas de Gran Canaria (ES)

( * ) Notice: Subject to any disclaimer, the term of this patent is extended or adjusted under 35 U.S.C. 154(b) by 0 days. days.

(21) Appl. No.: 14/225,704

(22) Filed: Mar. 26, 2014

(65) Prior Publication Data

US 2015/0174105 A1     Jun. 25, 2015

(30) Foreign Application Priority Data

Dec. 21, 2013 (ES) .................................. 201301177

(51) Int. Cl.
| | |
|---|---|
| *A61K 31/196* | (2006.01) |
| *A61K 31/4178* | (2006.01) |
| *A61K 9/00* | (2006.01) |

(52) U.S. Cl.
CPC ........ *A61K 31/4178* (2013.01); *A61K 9/0048* (2013.01); *A61K 31/196* (2013.01)

(58) Field of Classification Search
CPC .......................... A61K 31/196; A61K 31/4178
See application file for complete search history.

(56) References Cited

U.S. PATENT DOCUMENTS 8,524,758 B2 * 9/2013 Benozzi ........................ 514/397

OTHER PUBLICATIONS

Dovepress, Carreno et al., (Update on twice-daily bromfenac sodium sesquihydrate to treat postoperative ocular inflammation following cataract extraction), Apr. 2012.*

* cited by examiner

*Primary Examiner* — Zohreh A Fay
(74) *Attorney, Agent, or Firm* — John Alumit

(57) ABSTRACT

Ophthalmic composition for the correction of presbyopia. Composition consisting of 2% Pilocarpine, characterized by being diluted to 1% with sterile Balanced Salt Solution (BSS), obtaining 1% pilocarpine (2.5 ml)+bromfenac, 1.8 mgrs of bromfenac (2.5 ml)+sterile Balanced Salt Solution (BSS) (2.5 ml), finally obtaining eye drops of 7.5 ml. It is also possible to obtain a 1.5% and 2% pilocarpine.

6 Claims, No Drawings

OPHTHALMIC COMPOSITION FOR CORRECTING PRESBYOPIA

CROSS-REFERENCE TO RELATED APPLICATIONS

This disclosure claims the benefit of priority to ES Patent Application 201301177, filed 21 Dec. 2013, the disclosure of which is incorporated herein in its entirety.

FIELD OF THE INVENTION

The present invention relates to the pharmacological treatment of presbyopia.

BACKGROUND OF THE INVENTION

While presbyopia results from the loss of ability of the human eye to accommodate, which occurs throughout the population as of 40 years old, the problem is of sufficient magnitude to find different palliative solutions to reading glasses and viewing at short distances. As regards glasses, convex lenses are often used with an appropriate optical power usually ranging between 1 and 3 diopters. When a visual defect appears prior to the arousal of presbyopia making distance vision more difficult, for example myopia, it will be necessary to use two different glasses, one for near vision and one for distance vision or special progressive bifocal or multifocal lenses.

Contact lenses allow near and far vision by means of the same lens. Monovision is a method that consists in correcting one eye for distance vision and one for near vision. This procedure needs an adjustment period and sometimes it can interfere with depth perception. As far as surgery is concerned, there are several possibilities: the intraocular lens is a procedure in which the lens of the eye is removed and replaced by a multifocal intraocular lens. This procedure is often used in patients who have undergone surgery of eye cataract and are unwilling to use glasses after surgery for near vision. As in every surgery, complications may occur which, in this case, are very similar to those of cataract surgery; sometimes after the intervention light flashes are perceived and the patient may experience difficulty with night vision.

Corneal surgery can be performed by means of a laser technique intervention different for each eye, in such a way that an eye is adapted for near vision while the other for far vision, or monovision. It is also possible to treat the cornea by means of laser with the aim of simulating a bifocal or multifocal lens, but this technique has its limitations and it is difficult to obtain an adequate and stable correction over time, similar to the one achieved with multifocal intraocular lenses.

All these solutions to correct the problem of presbyopia show clear disadvantages for the patient who is forced to wear glasses, contact lenses, prostheses or to undergo undesired surgeries; this is why presbyopia problems can be solved, during the first time, from another approach, the medication approach.

Although no one has found an identical invention to the one described by the inventor, below we show the documents that have been found reflecting the state of the art related to it.

ES2304824A1 proposes a set of mask lenses for laser system to treat presbyopia, among others, using "Excimer Laser", which consists of a circular lens and a ring lens corresponding to the diameter of the pupil and/or iris of the application eyes, which are formed by contact lenses with maximum UV filter and PMMA transparent material. The complexity of the system contrasts with the lack of intervention of the proposed invention.

Document ES2351515T3 also describes a kit comprising a diversity of prostheses for contact with the sclera of an eyeball and adapted to expand the contacted sclera in order to increase the working distance of the eyeball ciliary muscle, where each of said diversity of prostheses includes a body having at least one end, with each prosthesis having means to fix such prosthesis within a respective cavity, surgically formed within the sclera of the eyeball; the attachment means include a surface provided by a concavity at the first end of the body.

Although more techniques for the correction of presbyopia are already known, such as patent ES2342684T3 or ES2228153T3, all these techniques are controversial, since they do not solve the mechanical problem of accommodation. Among these patents, we can found patent ES2337748A1 from the Argentinean inventor Dr. Jorge Luis Benozzi, whose ophthalmic compositions for the treatment of presbyopia consist of combinations of parasympathomimetics and non-steroidal anti-inflammatories in compositions wherein the parasympathomimetic agent is pilocarpine or its salts and the non-steroidal anti-inflammatory agent is selected from the group preferably consisting of diclofenac. The description of Dr. Benozzi's invention specifically makes reference to ophthalmic compositions of pilocarpine and a NSAID to use in the treatment of presbyopia, being pilocarpine in a preferred development of the invention in the form of hydrochloride and the NSAID as Diclofenac Sodium. The description continues, in the different treatment options, showing that Pilocarpine was used according to the studied group:

Group 1: 1% Pilocarpine Hydrochloride
Group 2: 2% Pilocarpine Hydrochloride
Group 3: 1% Pilocarpine Hydrochloride
Group 4: 2% Pilocarpine Hydrochloride In the 4 groups the NSAID was always 0.5% diclofenac sodium, at 6 hr intervals.

DESCRIPTION OF THE INVENTION

The ophthalmic composition for correcting presbyopia, object of the present invention is as follows: 2% Pilocarpine, diluted to 1% with sterile Balanced Salt Solution (BSS), obtaining 1% pilocarpine (2.5 ml)+bromfenac, 1.8 mgrs of bromfenac (2.5 ml)+sterile Balanced Salt Solution (BSS) (2.5 ml), finally obtaining eye drops of 7.5 ml.

The study carried out by the present invention is based on a composition distinct from Dr. Benotzzi's, as well as on other selection criteria as regards patients, exclusively including patients over 40 years old with evident signs of clear presbyopia with a refractive defect among −0.50 of myopia and +0.75 of hyperopia with a maximum astigmatism of −0.75, in addition to their corresponding age-based presbyopia.

Here, only those patients with the following characteristics were considered ideal candidates: an ACD (Anterior Chamber Diameter of the eye) greater than 2.5 mm, a White-to-White (horizontal diameter) greater than 11.4 mm and a value of photopic pupils higher than 3 mm. and of scotopic pupils lower than 6.5 mm, plus a correct convergence and binocularity and a density of the eye crystal lower than 25 measured with Pentacam.

Additionally, only the non-dominant eye has been always treated, a situation that is not reflected in the studies of Dr. Benozzi, although we have evidence that recommends the use in both eyes.

An essential difference with respect to diclofenac in Dr. Benozzi's invention is its permanence in the anterior chamber of the human eye over 12 hours; by means of this effect, it is possible to find measurable levels up to 24 hours in the major ocular tissues, which allows to use the compound preparation, an object of this invention, in a single daily application, improving, in that way, patient compliance to drug administration. Applying it once a day reduces drug exposure, while a significant clinical efficacy is still maintained.

The bromfenac significantly extends the parasympathomimetic action of pilocarpine, far beyond the diclofenac present in Dr. Benozzi's formula. The result is a significant increase in the depth of focus of the treated eye, which compensates for presbyopia in this large group of patients.

We may also use other concentrations of pilocarpine along with Bromfenac and the BSS for the unreleased and unpublished pharmacological correction of presbyopia, consisting of 7.5 ml eye-drops comprising 2% pilocarpine, diluted with sterile balanced salt solution (BSS), obtaining a 1.5% pilocarpine (2.5 ml) as well as bromfenac in the form of bromfenac sodium sesquihydrate (2.5 ml, 2.25 mgrs), to which 2.5 ml of sterile balanced salt solution (BSS) is added.

In a third different fulfillment, pilocarpine is also concentrated to 2% but with all other components, Bromfenac and BSS in the same concentrations.

Bromfenac is a nonsteroidal anti-inflammatory NSAID, cyclooxygenase inhibitor, essentially of COX-2, thereby blocking prostaglandin synthesis. By means of In Vitro procedures, it has been shown that bromfenac inhibits prostaglandin synthesis at the level of ciliary body and the iris.

Pilocarpine is a cholinergic drug of parasympathomimetic action that when applied to the ocular surface can cause: miosis and a sharp contraction of the circular and transverse fibers of the ciliary muscles, two processes that basically act on the mechanism of action of the accommodation, and produce a reduction in intraocular pressure. The third mechanism involved that benefits accommodation is a correct eye convergence.

The bromfenac sodium sesquihydrate efficiently pass through the human cornea, its concentrations in aqueous humor after instillation on the ocular surface remained for over 12 hours, with measurable levels until 24 hours in the major ocular tissues.

The BSS was proved by Simon et al in dry eyes as artificial tears compared with saline, Hypotears, Tears Naturale, Liquifilm, Bromhexine and eledoisin, and they found that it was the best one in terms of improving ocular surface testing and lacrimal gland stability; for this reason, it was considered as a third component in the formula, object of the present invention, due to its regeneration capacity and ocular surface stability; besides, it improves tolerance to the combination of pilocarpine and bromfenac.

DESCRIPTION OF A PREFERRED EMBODIMENT

A preferred embodiment of the ophthalmic composition for the correction of presbyopia, object of the present invention, can be obtained according to the following formulation: 2% Pilocarpine, diluted to 1% with sterile Balanced Salt Solution (BSS), obtaining 1% pilocarpine (2.5 ml)+bromfenac, 1.8 mgrs of bromfenac (2.5 ml)+sterile Balanced Salt Solution (BSS) (2.5 ml), finally obtaining eye drops of 7.5 ml.

Another composition is used for the pharmacological correction of prebyopia by means of 7.5 ml eye-drops comprising 2% pilocarpine, diluted with sterile balanced salt solution (BSS), obtaining a 1.5% pilocarpine (2.5 ml) as well as bromfenac in the form of bromfenac sodium sesquihydrate (2.5 ml, 2.25 mgrs), to which 2.5 ml of sterile balanced salt solution (BSS) is added.

The invention claimed is:

1. A 7.5 ml sample of an ophthalmic composition for the correction of presbyopia consisting of
    2.5 ml of 2% Pilocarpine, diluted to 1% with sterile Balanced Salt Solution;
    2.5 ml of 1.8 mg. to 2.25 mg. of bromfenac; and
    2.5 ml of sterile Balanced Salt Solution.
2. An ophthalmic composition for the correction of presbyopia, the composition comprising:
    an admixture of pilocarpine;
    bromfenac; and
    a sterile balanced salt solution,
wherein a 7.5 ml sample of the composition includes:
    0.3% to 2% pilocarpine;
    1.8 mg to 2.25 mg of bromfenac; and
    2.5 ml of a sterile balanced salt solution.
3. The ophthalmic composition of claim 2, wherein the composition includes 1% to 2% pilocarpine.
4. The ophthalmic composition of claim 3, wherein the composition includes 1.5% pilocarpine.
5. The ophthalmic composition of claim 2, wherein pilocarpine is pilocarpine hydrochloride.
6. The ophthalmic composition of claim 2, wherein the bromfenac is bromfenac sodium sesquihydrate.

* * * * *